US005719039A

United States Patent [19]
Dordick et al.

[11] Patent Number: 5,719,039
[45] Date of Patent: Feb. 17, 1998

[54] ENZYME-SURFACTANT ION-PAIR COMPLEX CATALYZED REACTIONS IN ORGANIC SOLVENTS

[75] Inventors: Jonathan S. Dordick, Iowa City, Iowa; Vikram M. Paradkar, Madison, Wis.

[73] Assignees: University of Iowa Research Foundation, Iowa City, Iowa; Biotechnology Research & Development Corp., Peoria, Ill.

[21] Appl. No.: 457,758

[22] Filed: Jun. 1, 1995

[51] Int. Cl.$^6$ .............................. C12P 1/00; C12P 21/06; C12N 11/04; C12N 9/00
[52] U.S. Cl. .......................... 435/41; 435/68.1; 435/182; 435/183; 435/195; 435/213
[58] Field of Search ............................. 435/41, 68.1, 182, 435/183, 195, 213

[56] References Cited

U.S. PATENT DOCUMENTS

| | | | |
|---|---|---|---|
| 4,870,016 | 9/1989 | Levesque et al. | 435/183 |
| 5,316,935 | 5/1994 | Arnold et al. | 435/222 |
| 5,413,935 | 5/1995 | Patel et al. | 435/280 |

FOREIGN PATENT DOCUMENTS 03-280880 12/1991 Japan.

OTHER PUBLICATIONS

Bruno et al., "Enzymatic Modification of Insoluble Amylose in Organic Solvents", Macromolecules, vol. 28, No. 25, pp. 8881–8883, (1995).
Bender et al. (1966) *J. Am. Chem. Soc.*, 88, "The Determination of the Concentration of Hydrolytic Enzyme Solutions: α-Chymotrypsin, Trypsin, Papain, Elastase, Subtilisin, and Acetylcholinesterase", pp. 5890–5913.
Tsuzuki et al. (1995) *J. Am. Oil Chem. Soc.*, 72(11), "Kinetics of Organic Solvent-Soluble and Native Lipase", pp. 1333–1337.
Biotechnol. Prog., (1992) vol. 8, pp. 259–267, "Designing Enzymes for use in Organic Solvents", Jonathan S. Dordick.
Biotechnol. Bioeng. (1992) vol. 39, pp. 392–397, "Organic Solvents Strip Water Off Enzymes", Lu Ann S. Gorman et al.
Genetic Engineering News, Apr. 15, 1995, "Biocatalysis Technology in the 1990's Offers Novel Tools and New Choices", Cort Wrotnowski, pp. 10–11.
Journal of the American Chemical Society, Jun. 1, 1994, vol. 116, No. 11, pp. 5009–5010, "Aqueous–like Activity of α–Chymotrypsin Dissolved in Nearly Anhydrous Organic Solvents", Vikram M. Paradkar et al.
Biotechnol. Bioeng., (1994,) vol. 43, pp. 529–540, "Mechanism of Extraction of Chymotrypsin into Isooctane at Very Low Concentrations of Aerosol OT in the Absence of Reversed Micelles", Vikram M. Paradkar et al.
The Journal of Biological Chemistry, Mar. 5, 1988, pp. 3194–3201, vol. 263, No. 7, "Enzymatic Catalysis in Nonaqueous Solvents", Aleksey Zaks et al.

Journal of the American Chemical Society, Dec. 29, 1993, vol. 115, No. 25, "Protein and Solvent Engineering of Subtilisin BPN' in Nearly Anhydrous Organic Media" Pramod P. Wangikar et al.
Biocatalysis (1990) vol. 3, pp. 227–233, "Enzymes in Organic Synthesis VII—Enzymatic Activity of HRP After Chemical Modification of the Carbohydrate Moiety", Didier Arseguel et al.
Journal of American Chemical Society, 1993, vol. 115, No. 4, pp. 1261–1264, "Structure and Stability of Insulin Dissolved in 1–Octanol", James Matsuura et al.
J. Chem. Soc. Chem. Commun., 1988, pp. 1392–1394 "A Lipid–coated Lipase as a New Catalyst for Triglyceride Synthesis in Organic Solvents", Yoshio Okahata et al.
Eur. J. Biochem., (1985), pp. 453–468, vol. 155, "Micellar Enzymology", Karel Martinek et al.
Biotechnol. Bioeng., (1992), vol. 40, pp. 91–102, "Mechanisms of Protein Solubilization in Reverse Micelles", S. F. Matzke et al.
Journal of the American Chemical Society, 1986, vol. 108, pp. 2767–2768, "Substrate Specificity of Enzymes in Organic Solvents vs. Water is Reversed", Aleksey Zaks et al.
Journal of the American Chemical Society, 1994, vol. 116, pp. 2647–2648, "Salts Dramatically Enhance Activity of Enzymes Suspended in Organic Solvents", Yuri L. Khmelnitsky et al.
Nature, Nov. 20, 1980, vol. 288, pp. 280–283, "A New Class of Angiotensin–converting Enzyme Inhibitors", A. A. Patchett et al.
Journal Chem. Soc. Faraday Trans., (1986), vol. 82, pp. 1755–1770, "Interfacial Tension Minima in Oil–Water–Surfactant Systems", Robert Aveyard et al.

(List continued on next page.)

*Primary Examiner*—Jon P. Weber
*Attorney, Agent, or Firm*—Michael A. Gollin; Spencer & Frank

[57] ABSTRACT

Organic enzyme solutions comprise an ion pair complex of an enzyme and a surfactant, and an organic solvent in which the enzyme-surfactant ion pair is dissolved. The solution has catalytic activity at least an order of magnitude greater than a suspension of an equal amount of the enzyme and organic solvent without ion pair complexes. The enzyme is preferably a hydrolase with an acyl transferase activity and the surfactant is Aerosol OT (sodium bis(2-ethylhexyl) sulfosuccinate) at low concentrations. The organic enzyme solution may be made by obtaining an aqueous solution of an enzyme at a pH of maximal enzyme activity, adding an ionic surfactant to the aqueous solution in an amount sufficient to form an ion pair, and extracting the enzyme-surfactant ion pair into an organic solvent phase without substantial formation of reversed micelles, to produce an anhydrous organic enzyme solution comprising the enzyme-surfactant ion pair dissolved in the organic solvent such that the enzyme retains native structure and substantial catalytic activity. Catalytic solutions according to the invention can be used to catalyze peptide synthesis from acyl donors and nucleophiles.

41 Claims, 2 Drawing Sheets

OTHER PUBLICATIONS

Biotechnology Progress, 1993, vol. 9, No. 2, pp. 199–203, "Affinity–Based Reverse Micellar Extraction and Separation (ARMES): A Facile Technique for the Purification of Peroxidase from Soybean Hulls", Vikram M. Paradkar et al.

The Journal of Physical Chemistry, 1988, vol. 92, No. 12, pp. 3505–3511, "Cytochrome c in Sodium Bis(2–ethylhexyl) Sulfosuccinae Reverse Micelles: Structure and Reactivity", P. Brochette et al.

The Journal of Physical Chemistry, 1993, vol. 97, pp. 3631–3640, "Solubilization Mechanism of Cytochrome c in Sodium Bis(2–ethylhexyl) Sufosuccinate Water/Oil Microemulsion", Motonari Adachi et al.

Biotechnology Progress, Mar. 1985, vol. 1, No. 1, pp. 69–74, "Protein Extraction Using Reverse Micelles", Kent E. Göklen et al.

Biotechnology Progress, 1992, vol. 8, No. 1, pp. 85–90, "Release and Recovery of Porcine Pepsin and Bovine Chymosin from Reverse Micelles: A New Technique Based on Isopropyl Alcohol Addition", A. Carlson et al.

Biotechnol. Bioeng., (1991), vol. 38, pp. 1302–1307, "Selective Separation and Purification of Two Lipases from *Chromobacterium viscosum* Using AOT Reversed Micelles", M. R. Aires–Barros et al.

Carrea et al. (1995) *Trends Biotechnol*, 13, "Role of Solvents in the Control of Enzyme Selectivity in Organic Media", pp. 63–70.

Jones (1986) *Tetrahedron*, 42(13), "Enzymes in Organic Synthesis", pp. 3351–3403.

ENZYME-SURFACTANT ION-PAIR COMPLEX CATALYZED REACTIONS IN ORGANIC SOLVENTS

BACKGROUND OF THE INVENTION 1. Field of the Invention

The present invention relates to enzyme-surfactant ion pairs with high catalytic activity and solubility in organic solution. More specifically, the invention relates to the solubilization of hydrolases in organic solvents without reversed micelles, and to enzyme-catalyzed reactions such as peptide synthesis with aqueous-like activity. 2. Related Art The longstanding desire to achieve catalysis in organic liquids has led to several approaches. Unlike aqueous-based enzymology, the vast majority of studies involving enzymes in nonaqueous media have employed biocatalyst suspensions. See reviews and references therein by (a) Klibanov, A. M. Trends Biochem. Sci. 1989, 14, 141; (b) Dordick, J. S. Enzyme Microb. Technol. 1989, 11, 194; (c) Dordick, J. S. Biotechnol. Prog., 1992 8, 259; and (d) Zaks, A.; Russell, A. J. J. Biotechnol. 1988, 8, 259. For example, some enzymes have been immobilized for suspension in organic solvents. Patel et al., U.S. Pat. No. 5,413,935; Persichetti et al., "Cross-linked enzyme crystals (CLECS) of thermolysin in the synthesis of peptides," J. Am. Chem. Soc. 1995. Suspended catalysts are limited by low mass transfer between the catalyst and substrate, diffusional limitations, masking of active centers, and difficulty in recovering insoluble products. Solubilization is preferred for applications where it is important to avoid these limitations.

Some efforts to solubilize enzymes in organic solvents have focused on chemical modification. Inada, Y.; Katsunobu, T.; Yoshimoto, T.; Ajima, A.; Matsushima, A.; Saito, Y., Trends Biochem. Technol., 1986, 4, 190; Arseguel, D.; Lattes, A.; Baboulene, M. Biocatalysis, 1990, 3, 227); Levesque et al., U.S. Pat. No. 4,870,016 (papain); and Arnold et al., U.S. Pat. No. 5,316,935 (subtilisin). However, chemical modification is tedious and often results in substantial enzyme inactivation.

Another approach has been the use of surfactants to form reversed micelles. (a) Martinek, K.; Levashov, A. V.; Khmelnitsky, Yu. L.; Klyachko, N. L; Berezin, I. V. Eur. J. Biochem. 1986, 155, 453; (b) Luisi, P. L.; Giomini, M.; Pileni, M. P.; Robinson, B. H. Biochim. Biophys. Acta 1988, 947, 209. Reversed micellar systems often consist of a high local water content in organic solvents (thereby destroying the true nonaqueous character of the organic solvent system), and result in excess surfactant that becomes a burden downstream.

It has also been shown that non-catalytic substances may form complexes with surfactants, but such complexes have not been demonstrated to have any catalytic activity. Matsuura, Powers, Manning, and Shefter, E. J. Am. Chem. Soc. 1993, 115, 1261; and Okahata and Ijiro, J. Chem. Soc. Chem. Commun. 1988, 1392.

The present inventors previously observed that chymotrypsin can be extracted from acidic aqueous solutions into organic solvents at very low surfactant concentrations (e.g., <2 mM) via ion-pairing of a surfactant with the protein. Paradkar and Dordick, Biotechnol. Bioeng. 1994, 43, 529 ("Paradkar & Dordick 1994"). It was shown in Paradkar & Dordick 1994 that an ion-paired complex of chymotrypsin and an anionic surfactant can be extracted into isooctane in the absence of reversed micelles. It was further shown that protein extraction can be optimized at pH 5 and ionic strength of 0.08M. Observations via active-site titration indicated that chymotrypsin retained nearly all of its catalytically active centers; and circular dichroism and fluorescence spectroscopy determinations suggested the enzyme was not structurally influenced by the extraction process.

This led to the general suggestion that the CT-surfactant complexes of Paradkar & Dordick 1994 may have direct application for preparing biocatalysts active and stable in homogeneous organic solutions.

SUMMARY OF THE INVENTION

It is an object of the invention to provide stable catalytic enzyme-surfactant complexes that can be dissolved in an organic solvent, maintain their native structure, and exhibit high catalytic activities approaching those of aqueous solutions, and exceeding the activity of a catalyst obtained by optimizing extraction variables.

It is another object of the invention to provide methods for enzyme catalysis in organic solutions.

It is a further object of the invention to catalyze peptide synthesis in organic solutions.

According to the invention, catalytic enzyme-surfactant ion pair complexes can be obtained by extraction from aqueous solution into organic solution, in substantially dehydrated form. These catalytic complexes can be obtained at maximal activity and can be used in a wide variety of catalytic reactions requiring homogeneous organic solutions. These complexes remain dissolved, maintain their native structure, and exhibit high catalytic activities which approach that in aqueous solutions.

The method of catalysis in an organic solvent according to the invention comprises:

(a) obtaining an ion pair complex of an activated enzyme and a surfactant, (b) dissolving the activated enzyme-surfactant ion pair complex in an organic reaction solvent without forming a significant quantity of reversed micelles, (c) adding to the organic reaction solvent a substrate for the enzyme, (d) allowing a sufficient time for the enzyme to catalyze conversion of the substrate to a product, and (e) recovering the product.

The method may be batch or continuous. Conversion of the substrate to the product may be substantially completed before the product is isolated. The enzyme may be precipitated from the organic solvent by removal of the surfactant from the enzyme-surfactant complex. The substrate can be added to, and the product isolated from the organic solvent solution while enzyme catalyzed conversion of substrate to product is continuing.

The substrate may comprise an acyl donor and a nucleophile, such as an amino acid, an amino acid ester, an N-blocked amino acid, an N-blocked amino acid ester, an amino acid amide, an N-blocked amino acid amide, a polypeptide, a polypeptide ester, an N-blocked polypeptide, an N-blocked polypeptide ester, a polypeptide amide, an N-blocked polypeptide amide, or a combination thereof.

For some hydrolases, the acyl donor is preferably a methyl or ethyl ester of tyrosine, tryptophan, alanine, or phenylalanine; a methyl or ethyl ester of a dipeptide or tripeptide containing tyrosine, tryptophan, alanine, or phenylalanine; or an N-benzoyl, N-acetyl, or N-carbobenzoxy derivative thereof; and the nucleophile is an amino acid amide.

The water content of the organic enzyme reaction solution preferably does not exceed the water saturation point for the organic solvent containing the surfactant. The molar ratio of water to enzyme in the organic reaction solvent may be kept less than about 75:1. Alternatively, the method may further comprise adding up to 0.2% v/v water to the reaction solvent.

To obtain the ion pair complex of the invention, a method comprises:

(1) forming a two-phase aqueous/organic system comprising an activated enzyme solution produced by dissolving an enzyme in an aqueous activating solution at a pH of maximal enzyme activity, an enzyme concentration of from about 1 µg/ml to about 10 mg/ml, and ionic strength less than about 80 mM, preferably less than 30 mM; an organic extraction solvent that is immiscible with water; and an ionic surfactant; the molar ratio of surfactant to enzyme in the two-phase system being in the range of about 15 to about 90 molecules of surfactant per 25,500 dalton enzyme, sufficient to form an enzyme-surfactant ion pair complex, and in a range of from about one tenth to substantially less than the ratio that would form reversed micelles in the organic solvent, (2) then agitating the two-phase system for a period sufficient to produce an ion pair complex of the activated enzyme and the ionic surfactant and to extract the ion pair complex directly from the aqueous solution into solution in the organic extraction solvent, without substantial formation of reversed micelles, (3) then separating the organic phase from the aqueous phase, whereby a homogeneous organic enzyme solution is obtained containing dissolved activated enzyme-surfactant ion pair complex and essentially no reversed micelles, he activated enzyme retaining native structure and having catalytic activity at least an order of magnitude greater than a suspension of an equal amount of the enzyme and organic solvent without surfactant.

The organic extraction solvent may be dried after extraction, or evaporated.

Preferably, the enzyme is α-chymotrypsin, the surfactant is AOT (aerosol OT, sodium bis(2-ethylhexyl) sulfosuccinate), the pH of the aqueous activating solution is from about 7.0 to about 8.5, the ionic strength is less than about 20 mM, the enzyme:surfactant ratio is about 1:30 and the enzyme surfactant ion pair has a catalytic efficiency $k_{cat}/K_m$ in isooctane for the transesterification of N-acetyl-L-phenylalanine ethyl ester with 1-propanol of greater than 3000 $M^{-1}S^{-1}$.

Preferably, when the volumes of aqueous solution and organic extraction solvent are about equal, the starting concentration of surfactant in the organic solvent is about 2 mM, and the starting concentration of the enzyme in the aqueous solvent is about 1 mg/ml.

The invention encompasses complexes in which the surfactant is cationic and the pH of maximum activity of the enzyme is above the pI.

A catalyst of the invention may be an essentially pure solid having water content of about 5% to about 10% by weight.

The enzymes include hydrolases with acyl transferase activity in organic solvent, catalytic antibodies, oxidoreductases, transferases, hydrolases, lyases, isomerases, lipases, ligases, a peroxidase catalyzing phenolic polymerizations, a tyrosinase catalyzing aromatic hydroxylations, and an alcohol dehydrogenase catalyzing stereoselective oxidation and reduction.

BRIEF DESCRIPTION OF THE DRAWINGS

The invention is better understood by reading the following detailed description with reference to the accompanying figures.

FIG. 2 illustrates the effect of water content on the product yield, using 5.5 mM acyl donor, 10 mM nucleophile, and 3.6 µM soluble alpha-chymotrypsin.

DETAILED DESCRIPTION OF THE PREFERRED EMBODIMENTS

Figure 1:
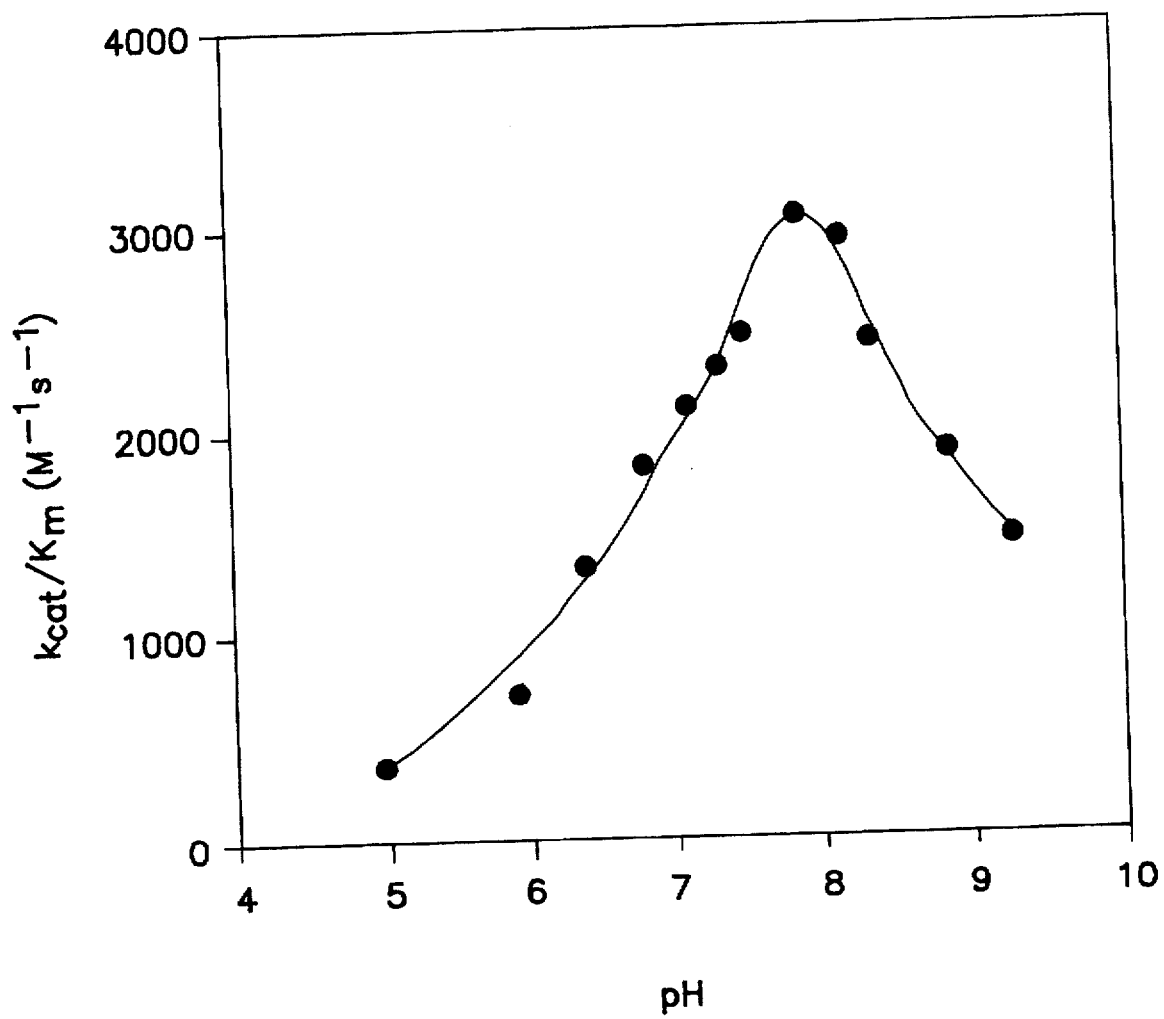
FIG. 1 illustrates the effect of aqueous phase pH used in alpha-chymotrypsin extraction on the resulting catalytic efficiency for the transesterification of Ac-L-Phe-OEt (N-acetyl-L-phenylalanine ethyl ester) with n-propanol. Values of $k_{cat}/K_m$ were determined as described in the legend to Table I.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

Enzyme-surfactant ion pairs in organic solutions can be obtained according to the invention with catalytic activity approaching the levels in aqueous solution.

Preferably, the enzyme is dissolved in the aqueous solution, the surfactant is dissolved in the organic solvent (most surfactants are only slightly soluble in water) and the two phases are then combined. See Paradkar and Dordick, 1994.

The method may preferably include selecting an enzyme; determining its pI and pH of maximum activity ($pH_{max}$) in aqueous solution; selecting an anionic surfactant if $pH_{max}$>pI, or a cationic surfactant if $pH_{max}$>pI; preparing an aqueous solution buffered to $pH_{max}$, and including any catalytically required metal ions, or cofactors, ions to provide desired ionic strength, and enzyme in a concentration up to about 10 mg/ml; selecting an organic solvent and a surfactant in a concentration of substantially less than the amount that would lead to substantial formation of reverse micelles, preferably less than about one half that amount (i.e. less than about 90 surfactant molecules, preferably between about 15 and 75, and most preferably about 30, for an average sized enzyme molecule having a molecular weight of about 25,500 daltons, which is completely enclosed by about 110 surfactant molecules), preferably in a range of about 1 to about 2.5 mM surfactant, most preferably about 1.5 mM to about 2 mM for each mg/ml enzyme present; selecting an extraction solvent that is immiscible in water, preferably having a attrition coefficient log P>0.68 (defined as the partitioning of the solvent between water and 1-octanol); and extracting an ion pair complex of the enzyme and surfactant from the aqueous phase solution into the extraction solvent.

Any ionic surfactant could be employed to form ion pairs according to the invention. Anionic surfactants such as AOT (aerosol OT, Sodium bis(2-ethylhexyl) sulfosuccinate) and SDS (sodium dodecyl sulfate), and quaternary ammonium salts may be used preferably with enzymes having a $pH_{max}$ below the pI. For enzymes forming ion pairs above the pI, cationic surfactants such as CTAB (cetyl trimethylammonium bromide) and DDAB (didodecylammonium bromide) may be employed.

The surfactant concentration is kept substantially below the level at which reversed micelles incorporating the enzyme would form (the reversed micelle ratio, or RMR), preferably no more than one half of the RMR, most preferably about one third that amount. The minimum surfactant/enzyme ratio forming soluble ion pairs according to the invention is about one tenth the RMR. For chymotrypsin and AOT in isooctane, the RMR is above about 110 molecules surfactant per molecule of enzyme, well above the preferred amounts of about 2 mM surfactant in the extraction solvent for each mg/ml enzyme in the aqueous solvent to be extracted.

In a preferred embodiment, the enzyme is alpha-chymotrypsin (CT) at about 1 mg/ml, the organic solvent is isooctane, and the surfactant is AOT in a concentration of less than about 2 mM. The pH of the aqueous activating solution is from about 7.0 to about 8.5, the ionic strength is less than about 20 mM, and the enzyme surfactant ion pair has a catalytic efficiency $k_{cat}/K_m$ in isooctane for the transesterification of N-acetyl-L-phenylalanine ethyl ester with 1-propanol of greater than 3000 per Molar per second. The enzyme:surfactant molar ratio is about 1:30. The activity of the extracted CT-AOT complex is about 2000 times that of chymotrypsin suspended in isooctane, and the activity is about an order of magnitude higher than chymotrypsin extracted from an aqueous solution at pH 5.0 where extraction is optimal as taught by Paradkar and Dordick 1994.

The surfactant concentration is low enough to avoid the formation of any significant quantity of reversed micelles, and the water concentration is no greater than the amount of water soluble in the organic solvent containing the surfactant.

Drying of the enzyme-containing isooctane phase by passing a stream of nitrogen gas through the organic liquid results in an extensively dehydrated soluble enzyme in isooctane, with a water content of about 0.03 µl/ml solvent. This soluble enzyme preparation with low surfactant content can then be mixed directly in a wide variety of organic solvents or collected by evaporating the solvent to form a solid preparation containing structural water only, with minimal exogenous water, about 5 to about 10 weight percent water total. The solid preparation can then be dissolved in a reaction solvent.

The catalysts and methods of the invention can be applied to most enzymes of the international classification, including oxidoreductases, transferases, hydrolases, lyases, isomerases, and ligases. Single chain enzymes are preferred because they can most easily be extracted with native structure, but any enzyme that can retain its quaternary, tertiary, and secondary structure through the extraction process may be employed. As used here, the term enzyme is meant to include any proteinaceous biocatalyst, including an antibody that has the activity of one of the enzyme classes when acting on an antigen in a non-aqueous solution. Proteins of molecular weight over about 200,000 daltons are too large to easily extract according to the invention.

Most preferred are hydrolases catalyzing acyl transfer. Preferred enzymes include α-chymotrypsin, subtilisin BPN' (from *Bacillus amyloliquefaciens*), subtilisin Carlsberg (from *Bacillus licheniformis*), and papain.

Organic solvents that may be used to extract soluble enzymes according to the invention include hydrophobic organic compounds like isooctane, octane, toluene, hexane, benzene, and the like; hydrophilic water miscible organic solvents are not preferred. In general, any organic solvent that is immiscible in water and has a log P greater than about 0.68, the partition coefficient of ethyl acetate, may be used for extraction. This includes the following classes of solvents: hydrocarbons, halogenated hydrocarbons, ethers, esters, aromatics, and so on.

The enzyme is extracted from an aqueous solution at the pH of maximal catalytic activity. For CT, that is greater than about pH 6.5, preferably about pH 7-8, most preferably pH 7.8. Surprisingly, the pH at which phase transfer is most efficient, as taught in Paradkar and Dordick 1994, is not the most desirable for enzyme activity. For CT, optimum extraction efficiency occurs from pH 4.0 to 6.5, preferably pH 5.0, but that gives an enzyme whose activity is about an order of magnitude less than the enzyme extracted at pH 7.8, with lower efficiency.

The enzyme concentration in the extraction medium is typically about 1 mg/ml, but may range from about 1 µg/ml to about 10 mg/ml. At higher protein concentration emulsification is a problem. The E/S (enzyme/surfactant) ratio may be determined in an organic solvent using methods taught in Paradkar & Dordick 1994, which is incorporated herein by reference. The amount of enzyme in the two phase solvent can be measured directly by standard methods and assays. The amount of complexed surfactant may be readily determined by the difference between the total surfactant in the organic solvent and the amount remaining as free surfactant after the enzyme is in solution. For example, as in Paradkar and Dordick 1994, rhodamine dye can be used to measure free AOT in the organic solvent spectrophotometrically.

The characteristic ratio that would form reversed micelles according to the invention may be termed the RMR or reversed micelle ratio, defined as the ratio of surfactant to enzyme in an organic extraction solvent at which significant numbers of reversed micelles form. The RMR may be approximated for a particular enzyme-surfactant-solvent system by calculation, empirical observation, or both. It should be noted that the RMR is only indirectly related to the critical micelle concentration (CMC) of the surfactant in the organic solvent (which is typically about 1 to as high as 3 mM in isooctane). The concentration of enzyme-surfactant (E-S) ion pair in organic solvent can far exceed the CMC. The presence of protein, in effect, raises the concentration of surfactant that would be needed to form micelles.

Reversed micelles form when a protein is fully enclosed in hydrophobic surfactant. Apparently, once all available protein is saturated with surfactant, then additional free surfactant begins to form reversed micelles, when the free surfactant reaches the CMC. Thus, the RMR is the concentration of surfactant needed to maintain a critical micelle concentration in a solvent containing extracted protein surfactant ion pairs. These CMCs are known or calculated from the literature.

The exact RMR depends on the surface area and surface charge density of the enzyme. In general, however, one can derive the RMR for a particular enzyme from the observed and calculated fact that the RMR for CT is about 110 molecules AOT per molecule enzyme. Thus, it may be stated that $$RMR = (X_o/MW_{CT}) \times (110) + CMC$$

in which $X_o$ is the concentration of enzyme extracted into the organic phase, in mg/ml, $MW_{CT}$ is the molecular weight of chymotrypsin in daltons (25,500), and 110 is the number of moles surfactant per mole of enzyme for a 25,500 MW enzyme (chymotrypsin). The critical micelle concentration for the given surfactant and solvent is added, to give RMR in moles per liter.

The constant of 110 may vary somewhat with the size and shape of the enzyme and the size of the surfactant. Therefore, it is desirable to confirm by experiment that no significant reversed micelles are forming.

The presence or absence of reversed micelles at a given ratio of surfactant to enzyme may be determined empirically such as by light scattering experiments according to known methods. Another test is to dilute the hydrophobic extraction solvent into a hydrophilic organic solvent such as tetrahydrofuran, which does not support reversed micelles.

For example, the RMR can be readily determined by a calibration test. A fixed enzyme concentration, e.g. 1 mg/ml in aqueous solvent, is extracted into an equal volume of extraction solvent containing surfactants ranging from e.g. 0.2 mM to 10 mM. Once the RMR is determined, a range of about one tenth to about half, preferably about one third the RMR is selected to form ion pairs. The key factor in the maximum amount of surfactant selected is avoiding reversed micelle formation. Therefore, it is possible to extract an enzyme according to the invention with up to about 90 of the 110 sites of a standard 25,500 dalton enzyme occupied by surfactant, which would correspond to about 85% of the RMR. In general, though, it is preferred to stay in the range below about half the RMR, corresponding most preferably to about one third to one half the occupied sites.

For example, for an enzyme of MW 25,500 in which 0.4 mg/ml extracts into an organic phase containing 2 mM surfactant, the RMR may be calculated as $0.4/25,500 \times 110+$ CMC=1.73 mM plus about 1 mM=2.73. For free micelles to form, the surfactant needs to fully occupy sites on the protein, and additional free surfactant is needed. Thus, according to the invention, a surfactant concentration of 2 mM will not lead to substantial formation of reversed micelles.

For extraction of 1 mg/ml of the protein, RMR=4.33+1= 5.33. Thus, a surfactant concentration up to about 4 mM will not lead to substantial formation of reversed micelles. This is well above the preferred amount of 2 mM.

For extraction of 10 mg/ml of the protein, RMR=43.3+ 1=44.3. Thus, a surfactant concentration up to about 30 mM will not lead to substantial formation of reversed micelles.

Even at low concentrations, the surfactant can partition into the aqueous phase from the organic phase, complex with the enzyme, and then the complex can partition into the organic phase. The ion pair is unstable and transient in the aqueous phase due to the weak ionic interactions that hold it together, but the complex is stable in the organic phase due to its hydrophobicity. The energy state in the dissociated condition is higher than as a complex. This phenomenon of thermodynamic stabilization occurs at the proper proportions of enzyme, surfactant, water, and organic solvent. Thus, the organic phase is, in effect, a thermodynamic collector for the catalytic ion pair complex according to the invention.

The lower limit of protein concentration is primarily based on inconvenience due to dilution and high volumes. The preferred concentration of surfactant at 1 µg/ml enzyme would be about 2 µm. At 10 mg/ml protein, the preferred surfactant concentration would be about 20 mM assuming nearly all enzyme is extracted.

Concentration of the enzyme may be accomplished during extraction by using a smaller volume of organic solvent than aqueous phase. For example, if the volume ratio of aqueous to organic phase is 10:1, about a 10 fold concentration of the enzyme will be achieved.

Appropriate buffers may be used to maintain the desired pH, such as bis-Tris propane-HCl buffer. The buffer should be selected for compatibility with the enzyme. The buffer may be in a concentration of from about 1 mM to about 200 mM, preferably about 10 mM.

Other components may be present in the aqueous solution to maximize the ultimate activity of the enzyme in organic solution or to increase the efficiency of phase transfer to the organic phase. For example, calcium chloride may be present to maintain the activity of a protease such as chymotrypsin, and to provide desired levels of ionic strength, in a concentration up to about 100 mM, preferably about 2 mM, and salts such as potassium chloride may be present for the latter purpose as well. The ionic strength for CT extraction is preferably less than about 50 mM, or less than 20 mM, and most preferably about 12 mM, when extraction is done to a pH 7.8 solution.

Further optional components of the aqueous phase include native components of the enzyme such as metal salts.

Extraction can preferably be achieved by mixing the aqueous enzyme solution with an equal volume of organic solvent, preferably isooctane containing a low level of the desired surfactant, e.g. AOT at 2 mM, and effecting phase separation. Agitation enhances mass transfer. The surfactant partitions into the aqueous phase from the organic phase, pairs with the protein and then either dissociates, or causes the protein to emulsify and precipitate, or according to the invention, causes the protein to partition into the organic phase where it is stable.

After extraction, the organic phase contains enzyme which may be analyzed spectrophotometrically or otherwise. The enzyme-surfactant combination of the invention does not include any significant presence of reversed micelles.

The ion pair complex according to the invention includes an enzyme of molecular weight up to about 200,000 daltons, pre-activated by dissolving it in an activating aqueous solution at a pH of maximum activity, and an ionic surfactant.

The surfactant and activated enzyme are complexed together as an essentially anhydrous enzyme-surfactant ion pair complex, the proportion of surfactant to pre-activated enzyme in the complex being sufficient to render the complex soluble in an organic solvent and in a range of from about one tenth to about half the proportion that would form reversed micelles in the organic solvent, and the complex, when dissolved in the organic solvent, retaining native structure and catalytic activity an order of magnitude higher than the activity of the enzyme suspended in the organic solvent.

The catalyst may further comprise an organic solvent in which the enzyme-surfactant ion pair is dissolved to form a homogeneous organic enzyme solution, the activated enzyme retaining native structure and having catalytic activity at least an order of magnitude greater than a suspension of an equal amount of the enzyme and organic solvent without surfactant. Following drying, the catalyst may be obtained as an essentially pure solid having water content of about 5% to about 10% by weight.

The molar ratio of water to enzyme may be from about 50 to 200 and is preferably less than about 75. This is less than the water typically present in lyophilized protein, and less than that trapped in reversed micellar enzyme systems.

The soluble enzymes of the invention are highly active in organic reaction solvents such as isooctane with activity approaching that in aqueous solutions. Reactions may also be run in water miscible organic solvents that are inappropriate for extraction, such as tetrahydrofuran, dimethylformamide, dimethylacetamide, ethanol, methanol, butanol, acetone, dioxane, and the like.

Most reactions that can be carried out using activated enzymes in suspension in organic solvents can be carried out according to the invention using enzyme mediated catalysis in a homogeneous organic solution.

Enzyme catalysis according to the invention, including such desirable reactions as degradation of toxic substances for bioremediation, and peptide synthesis, may be carried out in a large scale batch mode. Conversion of substrate to product is allowed to go to completion before product is recovered.

If the product is soluble, a substance may be added to precipitate the product separate from the enzyme. Alternatively, the enzyme can be precipitated. For example, a strong ion pairing substance like tributylammonium chloride may be added (if an anionic surfactant is used), which releases the surfactant from the enzyme, and leads to precipitation of the enzyme. Soluble product can then be obtained by evaporation.

A continuous reaction mode is desirable in certain applications. Substrate is added to the reaction mixture. As the reaction proceeds, the product is removed. For non-soluble product, the product precipitates out and may be collected. This approach is not feasible with enzymes in suspension. Substrate is continuously added until the enzyme catalyst is exhausted. Alternatively, ultrafiltration could be used in a continuous mode with soluble products substantially smaller than the enzyme surfactant ion pair complex, to remove product from the reaction vessel.

The method of the invention is suitable for large scale production of dipeptides, tripeptides, and longer polypeptides using alkyl esters of amino acids or short peptides as the acyl donor. N-terminal protection or blocking is preferred but not necessary. Nucleophiles may be carboxyl amides of amino acids or C-terminal amides of short peptides, and amino acids. Reactions are stereospecific for optically pure substrates.

The substrate may include an amino acid, an amino acid ester, an N-blocked amino acid, an N-blocked amino acid ester, an amino acid amide, an N-blocked amino acid amide, a polypeptide, a polypeptide ester, an N-blocked polypeptide, an N-blocked polypeptide ester, a polypeptide amide, an N-blocked polypeptide amide, or a combination thereof.

The substrate for peptide synthesis in homogenous organic solutions according to the invention may have the formula

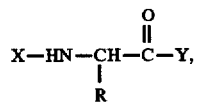

For the acyl donor,

R=side chains of amino acids;
X=any N-blocker, other amino acids, peptides, or H
Y=—OH, —NH$_2$, —O-alkyl, —O-aryl, —N-alkyl, N-aryl or other amino acids. As used here, the term aryl includes the presence of any substituents on the aryl ring, e.g nitrophenyl, and so on.

The same substrates may be used for the acyl acceptor (nucleophile), but X=H, and preferably Y=NH$_2$.

Preferably for CT or subtilisin, the acyl donor is a methyl or ethyl ester of tyrosine, tryptophan, alanine, or phenylalanine; a methyl or ethyl ester of a dipeptide or tripeptide containing tyrosine, tryptophan, alanine, or phenylalanine; or an N-benzoyl, N-acetyl, or N-carbobenzoxy derivative thereof; and the nucleophile is an amino acid amide.

Peptide synthesis may be carried out with roughly equimolar concentrations of acyl donor and nucleophile. A combination of non-polar and polar solvents may be used to achieve solubilization of the enzyme and the substrates. Minor amounts of water, up to about 0.1% v/v may be added to improve enzyme reactivity without competing with the acyl acceptor (nucleophile). The temperature may preferably range from about 0° C. to about 100° C., although certain thermally stable enzymes from hyperthermophilic organisms belonging to the kingdom of Archaea (such as Taq polymerase) may function at even higher temperatures. Preferably the temperature is about 30° C. Reaction times may range from about 10 minutes or less up to about six hours or more.

Other subtilisin enzymes that could be used include subtilisin DY from Bacillus subtilis, and related enzymes such is alkaline elastase YaB, minor extracellular protease, intracellular serine protease 1, thermitase, basic protease, extracellular protease, bacillopeptidase, cytolysin component A, epidermin protease, C5a peptidase, SK11 cell wall proteinase, extracellular serine protease, Ca-dependent protease, and alkaline protease.

Other proteases that are hydrolases in water may be used according to the invention, such as thermolysin, pepsin, papain, thrombin, and so on. Other enzymes suitable for catalysis while solubilized in organic solvents include: lipases, peroxidases, tyrosinases, glycosidases, nucleases, isomerases, aldolases, phosphatases, sulfatases, dehydrogenases, lyases, etc. Any enzyme may be employed provided it has some charged residues at the pH of maximal activity, so that it can ion pair with a surfactant. This includes some membrane-bound enzymes and most enzymes that typically exist in vivo in solution.

The surfactant masks the charges of the enzyme (e.g., for AOT the negative charge of the sulfonate group of the surfactant pairs with the positive charge of an amino group), and also conveys substantial hydrophobic character to the enzyme by virtue of the long hydrophobic hydrocarbon chains of the surfactant. Importantly, no covalent modification of the enzyme is required, and hydrophobic character is imparted to the enzyme in a mild and efficient manner.

Thus, most any enzyme may be employed according to the invention if it is able to retain its native components and structure in aqueous solution, complex with an anionic surfactant at a pH of maximum activity and partition into an organic phase as an ion pair, while still retaining native structure and components.

Cofactors for a particular enzyme may be added with the substrate to the reaction medium. Water-soluble cofactors could be added to the aqueous solution so that they bind to the enzyme as the latter is extracted.

Peptide synthesis reactions using organic soluble enzymes according to the invention are marked by several salient features including:

i) high conversions using nearly equimolar concentrations of both the acyl donor and the nucleophile;

ii) nearly quantitative yields; and iii) high reaction rates (and therefore relatively low enzyme concentrations required).

It is advantageous to keep the concentrations of the acyl donor and nucleophile close, to minimize waste of raw material. According to the invention, the concentrations are in a ratio of acyl donor to nucleophile of about 1:4 to about 4:1, preferably a range of about 1:2 to about 2:1, most preferably a range of about 1.5:1 to about 1:1.5. This is an advantage over other approaches to peptide synthesis that utilize high water contents. In such systems, a high (>10:1) ratio of donor/acceptor is employed to improve peptide yield.

The yields achieved may exceed 80%, meaning that only a small fraction of the ester donor is hydrolyzed in the reaction. In many cases the yield is 97% or greater. Yield can be greater than the percent conversion of the ester donor if the reacting ester donor is not hydrolyzed during the reaction.

Peptide synthesis according to the invention proceeds at high reaction rates, with most reactions being essentially completed in two to four hours. The homogeneous catalytic reaction solutions of the invention have definite advantages over suspensions and heterogeneous solutions (e.g., those containing significant quantities of reversed micelles with their inherent water pools).

Surprisingly, in a complex that has more surfactant than an enzyme suspension, but less than with reversed micelles, the solubility and activity are significantly enhanced as compared to both prior art systems.

Thus, the complexes of the invention allow full realization of the advantages of catalysis in organic solutions: e.g., increased solubility of nonpolar substrates, shifting thermodynamic equilibria to favor synthesis over hydrolysis, suppression of water-dependent side reactions, ease of product recovery, enhanced thermostability, and lack of microbial contamination.

This synthetic method could be run at liter scale or larger as a batch or continuous process. There are few problems with scale up because the use of a homogeneous solution essentially eliminates diffusional limitations and mass transfer limitations.

A recirculating process can be employed according to the invention. For example, a stream containing the initial acyl donor and nucleophile substrate is continuously added to a reaction vessel containing the solubilized enzyme. The reaction medium is circulated through a filtration device to continuously remove the dipeptide product, which is esterified or amidated and then returned to a reaction vessel as the acyl donor or nucleophile, respectively, for synthesis of a tripeptide. This process is repeated as desired to synthesize longer polypeptides. According to the invention, a peptide having as many residues as desired could be produced.

EXAMPLE 1

α-Chymotrypsin (CT) is easily extracted from an aqueous phase into isooctane containing a low concentration of surfactant (≦2 mM AOT) via the formation of ion pairs between the protein and the surfactant. The low surfactant ratio eliminates the formation of reversed micelles. Subsequent drying of the enzyme-containing isooctane phase results in an extensively dry (about 5% w/w on the enzyme) soluble enzyme in isooctane. This soluble enzyme preparation can then be dissolved in a wide variety of organic solvents. See Paradkar and Dordick, *J. Am. Chem. Soc.* 116, 5009–5010 (Jun. 1, 1994), which is incorporated herein by reference.

Soluble CT is highly active in isooctane, with a $k_{cat}/K_m$ for the transesterification of Ac-L-Phe-OEt (N-acetyl-L-phenylalanine ethyl ester) with n-propanol of $3,020 M^{-1}S^{-1}$ which is about 15% of that in aqueous buffer for Ac-L-Phe-OEt hydrolysis. The soluble enzyme is much more active than enzyme suspended in organic solvent—from about ten times to about 10,000 times more active in that particular solvent. With CT, the enzyme is about 2,500-fold more active than CT suspended in isooctane.

The catalytic turnover number is defined by $k_{cat}$. The Michaelis constant is defined by $K_m$. The ratio $k_{cat}/K_m$ reflects the catalytic efficiency for a particular substrate, in terms of the second order rate constant of the interaction of free enzyme and substrate.

Spectral analysis of soluble CT in hydrophobic organic solvents (i.e. solvents with log P>about 2) does not reveal any significant changes as compared to soluble CT in water. This shows that the soluble enzyme retains its native secondary and tertiary structure.

The highly active soluble CT was used for kinetically-controlled peptide synthesis resulting in efficient synthesis of dipeptides in yields approaching 100%. In addition to CT, subtilisin Carlsberg was dissolved in isooctane in a similar manner and shows a value of $k_{cat}/K_m$ for the transesterification of Ac-L-Phe-OEt and n-propanol of 68% of that for hydrolysis in aqueous buffer.

Extraction of a 1.1 mg/ml aqueous solution of α-chymotrypsin (CT), pH 7.8, into isooctane containing 2 mM Aerosol OT (AOT) results in the solubilization of 1.02 mg/ml (93% efficiency of extraction) CT. In a preferred approach, extraction was as follows.

The aqueous phase consisted of 10 mM bis-tris propane buffer, pH 7.8, containing 6 mM $CaC_2$ and 1.10 mg/ml CT. This phase was extracted with an equal volume of isooctane containing 2 mMAOT (sodium bis(2-ethylhexyl) sulfosuccinate) by stirring at 250 rpm at 25° C. for 2 min. The phases were allowed to settle and then centrifuged to effect clean phase separation. The concentration of CT in the organic phase was determined spectrophotometrically. Analysis of the dry enzyme preparation in isooctane by dynamic light scattering (Dawn Model B device from Wyatt Technology Co. (Santa Barbara, Calif.) using a 5 mW linear polarized He-Ne incident laser beam (632.8 nm)) showed a mean molecular size of 6.8 nm, consistent with a spherical complex of CT ion-pairing with AOT molecules.

Calculations of the number of AOT molecules associated per extracted CT molecule indicate that only about 30 surfactant molecules interact with the protein, a value too low for reversed micellar incorporation of the protein in isooctane.

The water content of the isolated isooctane phase following extraction is 0.3 μl/ml which can be reduced to 0.035 μl/ml by passing a stream of dry $N_2$ gas through the organic solvent. This results in an increased concentration of CT dissolved in isooctane of 1.12 mg/ml and a ratio of [water]/[CT]<50. This is far less than that obtained with CT suspended in isooctane without ion pair complexes (75-300). Zaks, A.; Klibanov, A. M. *J. Am. Chem. Soc.* 1986, 108, 2767. Dehydration can alternatively be achieved by thorough evaporation of the solvent to leave a powder of the enzyme-surfactant complex. Hence, the ion-pairing approach to CT solubilization results in a highly dehydrated, yet organic soluble enzyme preparation.

CT retains nearly all its catalytic sites when dissolved in organic solvents. Active site titration using N-transcinnamoylimidazole (NTC) in anhydrous isooctane resulted in the titration of 95% of the number of catalytic sites active in water within 90 min. Isooctane-soluble CT was titrated as follows: A two-fold molar excess (to enzyme) of N-transcinnamoylimidazole (NTC, Schonbaum, G. R.; Zerner, B.; Bender, M. L. *J. Biol. Chem.* 1961, 236, 2930) was dissolved in the solvent and the enzyme solution was incubated at 25° C. for 90 min with mild shaking at 50 rpm. The CT was precipitated from the reaction mixture by addition of 1% (v/v) methanol and the solids centrifuged.

The supernatant, containing unreacted NTC was analyzed by gas chromatography.

As shown in Table I, transesterification of Ac-L-Phe-OEt with 1-propanol in anhydrous isooctane gave a catalytic efficiency ($k_{cat}/K_m$)=3,020 $M^{-1}S^{-1}$ (which is within an order of magnitude of the $k_{cat}/K_m$ in aqueous buffer), and a $k_{cat}$ value nearly one-third as high as in aqueous buffer.

"Anhydrous" indicates solvents sufficiently dried such that the water content is <0.01%(v/v) which is the limit of the Karl-Fischer water determination method.

TABLE I

Activity of Soluble Chymotrypsin in Organic Solvents

| solvent | $k_{cat}/K_m$ ($M^{-1}s^{-1}$) | $k_{cat}$ ($s^{-1}$) | $K_m$ (mM) |
|---|---|---|---|
| isooctane | 3,020 | 16.6 | 5.5 |
| toluene | 320 | 3.8 | 12 |
| tert-Amyl Alcohol | 75 | 2.4 | 32 |
| tetrahydrofuran | 4.6 | 0.36 | 79 |
| tetrahydrofuran + 5 µl/ml $H_2O$[a] | 45 | 4.4 | 98 |
| aqueous buffer, pH 7.8[b] | 21,479 | 58.1 | 2.7 |
| isooctane (suspended)[c] | 1.26 | | |

[a]The solubility of CT in THF (up to 10 mg/ml) provides strong evidence that reversed micelles are not involved in solubilization, because THF cannot support reversed micelles.
[b]Hydrolysis of Ac-L-Phe-OEt was performed at pH 7.8 with a pH-Stat.
[c]As a comparative example, CT was lyophilized from the aqueous buffer (pH 7.8) containing 2.5 mg/ml Ac-L-Phe as described by Zaks and Klibanov, J. Biol. Chem. 1988, 263, 3194.

Unless otherwise stated, CT was in the soluble state and prepared by extraction from an aqueous buffer solution, pH 7.8, into isooctane, dried via $N_2$ gas, and diluted into the specific organic solvent. Transesterification of Ac-L-Phe-OEt with n-propanol employed an enzyme concentration of 1.25 µg/ml. Hydrolysis employed 4.0 µg/ml because the measurement for water reactions (hydrolysis) used a continuous measurement pH-STAT. Thus real-time measurements were possible. For transesterification, gas chromatography (GC) was used and this could not be done continuously. Hence, time points were used and the reaction was slowed down to conform to the GC limitations.

The solvents contained no more than 0.03% (v/v) water as measured by Karl-Fischer titration, except for isooctane which has no more than 0.01% (v/v) water.

Values for $k_{cat}/K_m$ were determined by nonlinear fit of the kinetic data and represent averages of triplicate measurements with standard deviations in each case of less than 5%. Initial rates of formation of N-acetyl-L-phenylalanine propyl ester were determined by gas chromatography (530-µm fused silica gum (Hewlett-Packard)). No reaction was observed with CT pre-inactivated by phenylmethanesulfonyl fluoride (PMSF, 0.3 mM) (Gold, A. M.; Farney, D. Biochemistry 1964, 3, 783). Saturation kinetics could not be determined for reactions with CT suspended in isooctane as the solubility limit for the substrate in this solvent is substantially below the $K_m$ of the enzyme.

Controlled experiments surprisingly establish that CT activity as an ion-pair complex dissolved in an organic solvent strongly depends on the pH of the aqueous solution used in the protein extractions (FIG. 1). An important aspect of the invention is that the pre-activation is applicable to all enzymes having a specific pH optimum or pH range of maximal activity.

According to the invention, it has been determined that the improved activity of ion pair complexes dissolved in organic solvents as compared to suspended enzymes is further enhanced by pre-activation in an activating aqueous solution. As shown in FIG. 1, the catalytic efficiency of CT activated at pH 7.8 was about 10 times higher (about 3000 $M^{-1}S^{-1}$) than CT extracted at pH 5, about 5 times higher than CT extracted at pH 6, and about twice that of CT extracted at pH 6.5. Above the pH of 8, the activity drops again, so the activity of enzyme extracted at pH 9 is about that for pH 6.5. Thus, CT can be pre-activated by extraction from an aqueous solution having a pH within about 1 unit of the pH maximum, preferably at the pH maximum.

The phenomenon of inorganic memory was previously observed in the context of suspended enzymes which are dried (lyophilized) and then mixed with an organic solution. Zaks, A.; Klibanov, A. M. J. Biol. Chem. 1988, 263, 3194. Pre-activation according to the invention, in contrast, occurs when an enzyme surfactant ion pair complex forms in the pre-activation aqueous solution and then partitions directly into the organic phase. Direct extraction of pre-activated enzyme to the organic phase, according to the invention, is preferable not only because the enzyme goes into solution rather than suspension, but also because it avoids the possibility that the activated enzyme might be destabilized or disrupted by lyophilization or subsequent treatment.

Moreover, pre-activation is contrary to the teachings of Paradkar & Dordick 1994, p. 531, because the extraction yield at the pH max is significantly lower than at pH 5 which was the optimal extraction pH observed in the prior art. Pre-activation may lower the extraction yield. In conjunction with pre-activation according to the invention, therefore, it is desirable to increase the extraction yield at the pH max to compensate, e.g. by reducing the ionic strength.

CT is also soluble and active in isooctane and several other anhydrous solvents (Table I). In all cases, the activity of the soluble enzyme is at least three times higher than the activity for suspended CT in isooctane, and three orders of magnitude higher when in isooctane.

The increased catalytic activity of CT in solution as compared to suspension is unlikely to be due to a relaxation in diffusional limitations inherent in heterogeneous suspensions. Such limitations would not be expected to contribute more than an order of magnitude in increased activity. Khmelnitsky, Yu. L.; Welch, S. H.; Clark, D. S.; Dordick, J. S. J. Am. Chem. Soc. 1994, 116, 2657.

Instead, the soluble CT preparations in organic solvents appear to retain more native structure than their heterogeneous counterparts. Spectroscopic analyses indicate that CT retains nearly all of its native secondary and tertiary structure while dissolved in organic solvents, perhaps as a result of the potential stabilizing effects of ion-pairing. Virtually no differences were observed for CT dissolved in isooctane or in aqueous buffer for the uv spectrum (230–310 nm) and the circular dichroism spectrum (220–300 nm). No significant differences were observed in the fluorescence spectra of CT ($\lambda$=295 nm; $\lambda$=328 nm as maxima) in all solvents (including water) listed in Table I. Thus, little secondary or tertiary structural differences in CT were evident between aqueous buffer and organic solvents.

The lower activity in hydrophilic solvents such as tetrahydrofuran (Table I) is consistent with observations of suspended enzymes in similar solvents and may be due to the stripping of water off the soluble enzyme. Gorman, L. S.; Dordick, J. S. Biotechnol. Bioeng. 1992, 39, 392.

Lower values of $k_{cat}/K_m$ may also result from the increased ground-state stabilization of the substrate in more hydrophilic solvents, thereby increasing the apparent $K_m$ of the enzymatic reaction. (a) Ryu, K.; Dordick, J. S.

*Biochemistry*, 1992, 31, 2588; and (b) Wangikar, P. P.; Graycar, T. P.; Estell, D. A.; Clark, D. S.; Dordick, J. S. *J. Am. Chem. Soc.* 1993, 115, 12231. It is important to note that the $K_m$ (apparent) for Ac-L-Phe-OEt increases from 5.1 to 79 mM in going from isooctane to THF, thus partially explaining the drop in $k_{cat}/K_m$ in THF as compared to isooctane.

EXAMPLE 2

The high catalytic activity of solubilized CT-AOT ion pair complexes was applied to the facile synthesis of dipeptides (Table II).

TABLE II

Peptide Synthesis Catalyzed by Soluble Chymotrypsin[a]

| ester donor | nucleophile | Reaction Time (h) | Conversion[b] (% of ester donor) | Yield[c] (%) |
|---|---|---|---|---|
| Bz-Tyr-OEt | Phe-NH$_2$ | 2 | 96 | 99 |
| Bz-Tyr-OEt | Tyr-NH$_2$ | 2 | 93 | 98 |
| Bz-Tyr-OEt | Leu-NH$_2$ | 2 | 91 | 97 |
| Bz-Tyr-OEt | Pro-NH$_2$ | 4 | 87 | 85 |
| Ac-Trp-OEt | Phe-NH$_2$ | 2 | 94 | 98 |
| Bz-Ala-OMe | Phe-NH$_2$ | 2 | 92 | 98 |
| Bz-Ala-OMe | Pro-NH$_2$ | 6 | 65 | 84 |
| Ac-Phe-OEt | Phe-NH$_2$ | 2 | 98 | 99 |
| Ac-Phe-OEt | Leu-NH$_2$ | 2 | 96 | 94 |

[a]The reactions were performed in 1 ml isooctane containing 30% (v/v) THF (to aid in solubility of the substrates) and 5 mM L-ester, 7.5 mM L-amino acid amide, and 0.15 mg/ml soluble CT. The reactions were terminated by addition of 0.1 ml glacial acetic acid and dried. The residue was redissolved in 25 mM triethylammonium phosphate buffer (pH 3.0) containing 30% (v/v) CH$_3$CN and analyzed by reversed phase HPLC (C$_{18}$ μBondapak, Waters) with the same buffer as eluant. Ac and Bz represent N-acetyl and N-benzoyl, respectively.
[b]Total conversion of ester substrate.
[c]With respect to dipeptide formed versus total product (dipeptide + hydrolysis) formed.

In aqueous solution, CT has a preference for bulky, hydrophobic P$_1$ substrates. (Blow, D. M. *Acc. Chem. Res.* 1976, 9, 145). However, according to Table II, relatively high conversions were obtained for synthesis of N-benzoyl-Ala-Pro-NH$_2$, which is a non-bulky substrate. Ala-Pro is an intermediate in the synthesis of the antihypertensive drug enalapril (Patchett, A. A. et al., *Nature*, 1980, 288, 280.) Therefore, this synthetic pathway has commercial potential.

According to the invention, the simple ion-pairing of a common surfactant to α-chymotrypsin results in a highly active biocatalyst soluble in anhydrous organic solvents. These findings may be extended to other enzymes and surfactants.

For example, subtilisin Carlsberg dissolved in isooctane is also highly active for the transesterification of Ac-L-Phe-OEt with n-propanol ($k_{cat}/K_m$=4,160 M$^{-1}$S$^{-1}$, ca. 68% of the value in aqueous buffer). Thus, the approach of the invention described herein appears to be general, predictable, yet simple to perform, and results in highly active enzyme preparations for fundamental and applied uses.

EXAMPLE 3

CT-catalyzed peptide synthesis was extended to gram-scale synthesis: Incubation of 5 mmol N-benzoyl-L-tyrosine ethyl ester (Bz-L-Tyr-OEt) with 7.5 mmol L-Phe-NH$_2$ in 0.1 L of isooctane (containing 30%, v/v, tetrahydrofuran (THF)) resulted in the synthesis of 1.76 g of Bz-Tyr-Phe-NH$_2$ (isolated yield of 82%) with no hydrolysis product. THF was added to increase the solubility of the substrates in isooctane. Analysis of the dipeptide indicated the presence of 93 μg AOT per g peptide. This is less than 0.01% surfactant, and so the peptide is 99.99% pure. Thus, very little excess surfactant is entrained in the final product, and highly pure peptides may be obtained.

EXAMPLE 4

This example shows a general method for preparing solubilized enzymes in their catalytically optimized form. The general method for solubilization of enzymes into isooctane is given for subtilisin BPN' (from *Bacillus amyloliquefaciens*) and the extraction results are below the method.

Subtilisin BPN' was extracted from a 1 mg/ml aqueous solution (pH 7.8) into isooctane containing 2 mM Aerosol OT (AOT), yielding 40% extraction. Subtilisin has a molecular weight of 27,500. The pI of the enzyme is 9.4 and maximal activity is at pH 7.8, so an anionic surfactant was applied. The aqueous phase consisted of 10 mM bis-tris propane buffer, pH 7.8, containing 2 mM CaCl$_2$ and 1 mg/ml subtilisin. This phase was extracted with an equal volume of isooctane containing 2 mM AOT (sodium bis(2-ethylhexyl) sulfosuccinate) by stirring at 250 rpm at 25° C. for 2 min. The phases were allowed to settle and then centrifuged to obtain clean phase separation. Drying of the organo-soluble enzyme, by bubbling N$_2$ through the solution, resulted in dried enzyme-AOT ion-paired complex, which can then be diluted in any organic solvent of choice (e.g. THF, acetone, t-amyl alcohol etc.). The concentration of subtilisin in the organic phase was determined spectrophotometrically.

Extraction Results

For subtilisin BPN, the results were as follows: Aqueous phase: 1 mg/ml subtilisin in 10 mM Bis-Tris propane-HCl buffer, pH 7.8, 2 mM CaCl$_2$ Organic phase: 1 ml isooctane containing 2 mM AOT Extraction Yield: 0.4 mg/ml subtilisin in organic phase

EXAMPLE 5

This example provides extraction data for subtilisin Carlsberg (from *Bacillus licheniformis*). This enzyme has pI of 8.5 and maximum activity at about pH 7.8. The solubilization method and assays were the same as in Example 4.

Extraction results

Aqueous phase: 1 mg/ml subtilisin in 10 mM Bis-Tris propane-HCl buffer, pH 7.8, 2 mM CaCl$_2$ Organic phase: 1 ml isooctane containing 2 mMAOT Extraction Yield: 0.3 mg/ml subtilisin in organic phase

EXAMPLE 6

This example provides extraction data for α-chymotrypsin. The solubilization method and assays were the same as in Example 4. This enzyme has a pI of about 8.0 and maximum activity at about 7.8. The results were as follows:

Extraction Results

Aqueous phase: 1 mg/ml α-chymotrypsin in 10 mM Bis-Tris propane-HCl buffer, pH 7.8, 2 mM CaCl$_2$ Organic phase: 1 ml isooctane containing 2 mM AOT Extraction Yield: 0.93 mg/ml chymotrypsin in organic phase

EXAMPLE 7

This example provides extraction data for papain. Papain has a pI of about 8.75 and maximal activity at pH 7.8.

Manganese and potassium chloride were added to the aqueous solution because they are helpful to maintain activity. Extraction was performed as in Example 4 at pH 7.8 because this is a pH of maximal activity.

Extraction Results

Aqueous phase: 0.5 mg/ml papain in 10 mM Bis-Tris propane-HCl buffer, pH 7.8, 3 mM $CaCl_2$, 3 mM $MnCl_2$, 1 mM KCl Organic phase: 1 ml isooctane containing 2 mM AOT Extraction Yield: 0.35 mg/ml papain in organic phase

EXAMPLE 8

Soybean peroxidase has a pI of about 4 and a $pH_{max}$ about 5–7. Therefore, the enzyme has a net negative change in the activating solution, and forms active catalytic ion pairs with a cationic surfactant under the same extraction conditions as in Example 4.

EXAMPLE 9

This example compiles peptide synthesis data using chymotrypsin as catalyst. See Table III. Table III shows the acyl donor and the nucleophile (acceptor) which react to form the product. The reaction time and yield are listed.

reaction mixture was incubated at room temperature for a certain period of time. Final concentrations of the reactants in the reaction mixture were: 5.0–6.5 mM acyl donor, 7.5–10.0 mM nucleophile, α-chymotrypsin 3.5 µM. The reaction was terminated by addition of 10% v/v acetic acid, the mixture was dried, the residue was redissolved in 70:30 mixture of 0.1% trifluoroacetic acid (TFA) solution in water and acetonitrile and analyzed by reversed phase HPLC (C18 µBondapak column, Waters) using 0.1% TFA solution in water and acetonitrile mixture as eluant.

The first nine entries under (A) are repeated from Table II here for comparison, and showing the product. The next group of examples under (B) shows relatively low yields (38–51%) where the nucleophile is $Leu-NH_2$ and the acyl donor is the methyl ester of N-CBZ-Val-Tyr, N-CBZ-Ala-Phe, N-CBZ-Val-Trp. To enhance the enzyme activity, 1 µl/ml of water was added to the reaction mixture to activate the enzymatic reaction. The last three entries in (B) show that this minor amount of water surprisingly increased the yields to the 76–97% range, in shorter reaction times. The addition of 0.1% water to the reaction medium is believed to enhance activity by maintaining the active structure of the chymotrypsin, and yet is not present at high enough concentrations to compete stoichiometrically with the nucleophile substrate, which leads to hydrolysis.

TABLE III

Peptide Synthesis Catalyzed by Soluble Chymotrypsin

| Acyl donor | Nucleophile | Product | Reaction time, min | Yield (%) |
|---|---|---|---|---|
| A. | | | | |
| Bz-Tyr-OEt | Phe-$NH_2$ | Bz-Tyr-Phe-$NH_2$ | 120 | 99 |
| Bz-Tyr-OEt | Tyr-$NH_2$ | Bz-Tyr-Tyr-$NH_2$ | 120 | 98 |
| Bz-Tyr-OEt | Leu-$NH_2$ | Bz-Tyr-Leu-$NH_2$ | 120 | 97 |
| Bz-Tyr-OEt | Pro-$NH_2$ | Bz-Tyr-Pro-$NH_2$ | 240 | 85 |
| Ac-Trp-OEt | Phe-$NH_2$ | Ac-Trp-Phe-$NH_2$ | 120 | 98 |
| Bz-Ala-OMe | Phe-$NH_2$ | Bz-Ala-Phe-$NH_2$ | 120 | 98 |
| Bz-Ala-OMe | Pro-$NH_2$ | Bz-Ala-Pro-$NH_2$ | 360 | 84 |
| Ac-Phe-OEt | Phe-$NH_2$ | Ac-Phe-Phe-$NH_2$ | 120 | 99 |
| Ac-Phe-OEt | Leu-$NH_2$ | Ac-Phe-Leu-$NH_2$ | 120 | 94 |
| B. | | | | |
| CBZ-Val-Tyr-OMe | Leu-$NH_2$ | CBZ-Val-Tyr-Leu-$NH_2$ | 120 | 38 |
| CBZ-Ala-Phe-OMe | Leu-$NH_2$ | CBZ-Ala-Phe-Leu-$NH_2$ | 120 | 50 |
| CBZ-Val-Trp-OMe | Leu-$NH_2$ | CBZ-Val-Trp-Leu-$NH_2$ | 120 | 51 |
| CBZ-Val-Tyr-OMe | Leu-$NH_2$ | CBZ-Val-Tyr-Leu-$NH_2$ | 25 | 97[a] |
| CBZ-Ala-Phe-OMe | Leu-$NH_2$ | CBZ-Ala-Phe-Leu-$NH_2$ | 90 | 81[a] |
| CBZ-Val-Trp-OMe | Leu-$NH_2$ | CBZ-Val-Trp-Leu-$NH_2$ | 90 | 76[a] |
| CBZ-Val-Phe-OMe | Leu-$NH_2$ | CBZ-Val-Phe-Leu-$NH_2$ | 90 | 90[a] |
| CBZ-Ile-Phe-OMe | Leu-$NH_2$ | CBZ-Ile-Phe-Leu-$NH_2$ | 90 | 49[a] |
| C. | | | | |
| CBZ-Val-Tyr-OMe | L-Leu-$NH_2$ | CBZ-Val-Tyr-L-Leu-$NH_2$ | 60 | 50[a] |
| CBZ-Val-Tyr-OMe | L-Phe-$NH_2$ | CBZ-Val-Tyr-L-Phe-$NH_2$ | 60 | 21[a] |
| CBZ-Val-Tyr-OMe | D-Leu-$NH_2$ | CBZ-Val-Tyr-D-Leu-$NH_2$ | 60 | 67[a] |
| CBZ-Val-Tyr-OMe | D-Phe-$NH_2$ | CBZ-Val-Tyr-D-Phe-$NH_2$ | 60 | 68[a] |
| CBZ-Val-Tyr-OMe | L-Leu-$NH_2$ | CBZ-Val-Tyr-L-Leu-$NH_2$ | 60 | 19 |
| CBZ-Val-Tyr-OMe | L-Phe-$NH_2$ | CBZ-Val-Tyr-L-Phe-$NH_2$ | 60 | 8 |
| CBZ-Val-Tyr-OMe | D-Leu-$NH_2$ | CBZ-Val-Tyr-D-Leu-$NH_2$ | 60 | 24 |
| CBZ-Val-Tyr-OMe | D-Phe-$NH_2$ | CBZ-Val-Tyr-D-Phe-$NH_2$ | 60 | 15 |
| D. | | | | |
| Tyr-OEt[b] | Leu-$NH_2$ | Tyr-L-Leu-$NH_2$ | 10 | 89 |

[a]The reaction mixture contained 1 µl/ml water
[b]Unblocked (not N-protected) acyl donor was used.

The reaction was performed in isooctane-tetrahydrofuran (THF) 70:30 mixture. Acyl donor and nucleophile were dissolved in THF, then isooctane and soluble α-chymotrypsin solution in isooctane were added and the Polar solvents may provide similar structural stabilization without addition of water, or further solubilization of substrates. For example, isoproponol or other alcohols could be used in the reaction medium.

Stereospecific catalysis is shown under (C). As can be seen, the addition of 1 µl/ml of water to the reaction medium increased the yields from the 8–24% range to the 21–68% range. Surprisingly, the D-Leu and D-Phe isomers were more reactive than their L-counterparts.

Finally, under (D), an unblocked amino acid ester was used as an acyl donor in the reaction. The quick reaction time and high yield demonstrate the feasibility of soluble enzyme catalysis using acyl donors without N-blockers. This is important as it is often desired to use unblocked amino acids as donors and acceptors due to their lower costs.

Unblocked acyl donors might include an amino acid or peptide methyl or ethyl ester. Unblocked Nucleophiles would include an amino acid itself.

EXAMPLE 10

Figure 2A:
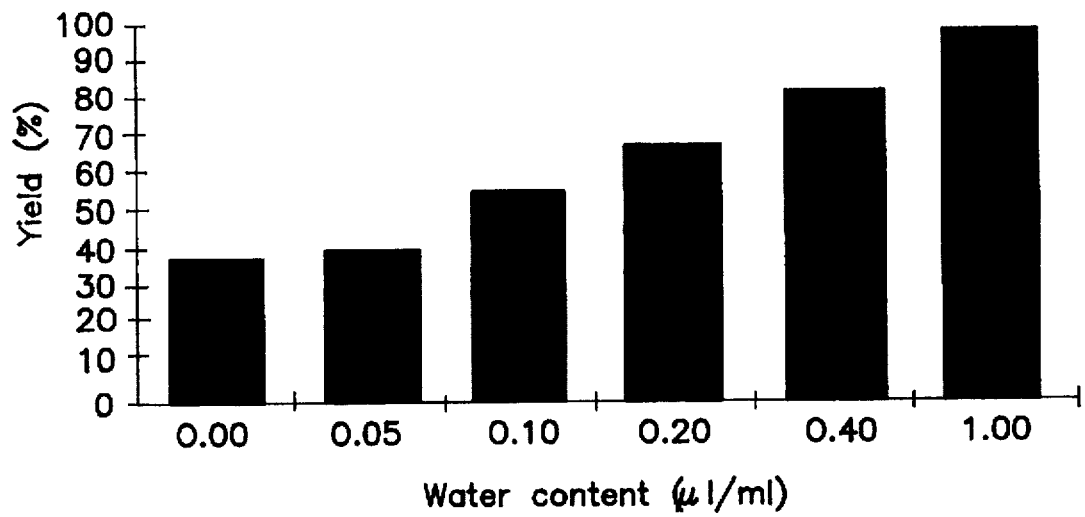
In FIG. 2a the acyl donor is Bz-Tyr-OEt (N-benzoyl tyrosine ethyl ester), the nucleophile is LeuNH$_2$ (leucine amide, in which the carboxyl group is blocked with an amino group to form an amide), and the product is Bz-Tyr-LeuNH$_2$ (N-benzoyl tyrosine leucine amide).
Figure 2B:
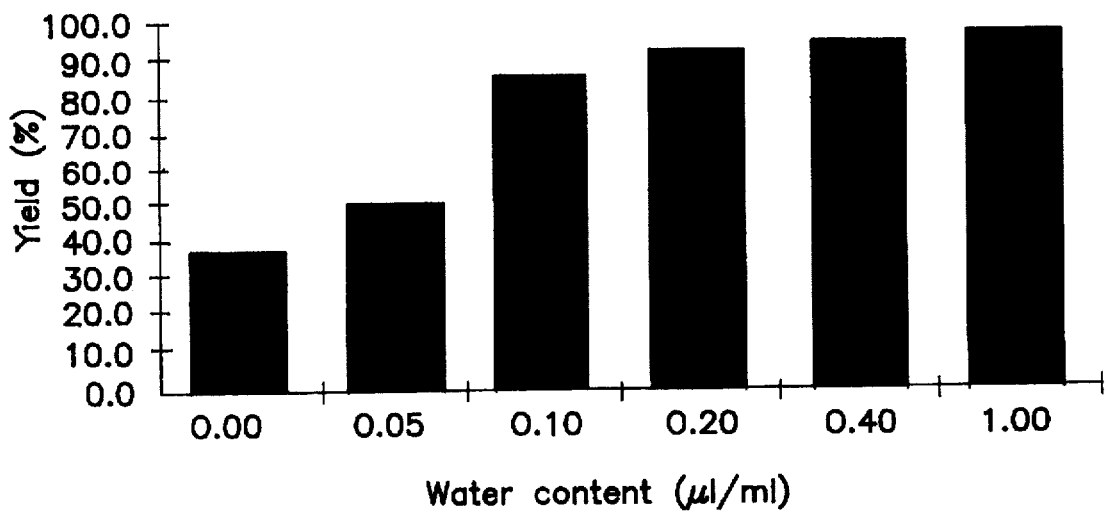
In FIG. 2b the acyl donor is the N-blocked dipeptide CBZ-Val-Tyr-OMe (N-carbobenzoxy-valine-tyrosinemethylester), the nucleophile is LeuNH$_2$, and the product is the N-blocked tripeptide CBZ-Val-Tyr-LeuNH$_2$.

This example demonstrates the effect of added water on reactions catalyzed by chymotrypsin obtained as in Example 1. Two bar graphs for different reactions catalyzed by chymotrypsin are shown in FIG. 2. The reactions are given above each graph and the effect of added water concentration (from 0 to 1 µl/ml) on each reaction yield is given. With N-benzoyl-L-tyrosine ethyl ester and 1-leucine amide, the maximal yield was obtained at 1 µl/ml. For N-carbobenzoxy-Val-Tyr methyl ester, maximal yields were obtained with water content as low as 0.2 µl/ml. It is clearly demonstrated that addition of very small concentrations of water (1 µl/ml=0.1% V/V) is capable of increasing the reaction yield.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. Other enzymes, surfactants, solvents, and substrates may be used in similar manner or using minor variations according to techniques known in the art. It is therefore to be understood that, within the scope of the claims and their equivalents, the invention may be practiced otherwise than as specifically described.

What is claimed is:

1. A method of catalysis in an organic reaction solvent, comprising the steps of:
  (a) obtaining a pre-activated enzyme-surfactant ion pair complex comprising an enzyme and an ionic surfactant capable of forming an ion pair complex with the enzyme, the complex having catalytic efficiency at least an order of magnitude grater than a suspension of an equal amount of the enzyme in the organic reaction solvent without surfactant, and produced by a process comprising dissolving the enzyme in an aqueous solution at a pH of maximal enzyme activity and agitating the enzyme-containing aqueous solution with an aqueous-immiscible organic extraction solvent and the dissolved ionic surfactant so as to extract the enzyme into the organic extraction solvent as a surfactant-enzyme ion pair complex, the ratio of surfactant to enzyme being less than that necessary to form reversed micelles,
  (b) combining the enzyme-surfactant ion pair complex with an organic reaction solvent,
  (c) adding to the organic reaction solvent at least one substrate for the enzyme, and
  (d) allowing a sufficient time for the enzyme to catalyze conversion of the substrate to a product, and recovering the product.

2. The method of claim 1 wherein step (a) comprises:
  (1) forming a two-phase aqueous/organic system comprising (i) a pre-activated enzyme solution produced by dissolving the enzyme in the aqueous solution at a pH of maximal enzyme activity, the aqueous solution having an enzyme concentration of from about 1 µg/ml to about 10 mg/ml, and ionic strength less than about 80 mM, (ii) an organic extraction solvent that is immiscible with water, and (iii) an ionic surfactant, the molar ratio of surfactant to enzyme in the two-phase system being sufficient to form an enzyme-surfactant ion pair complex, and substantially less than that necessary to form reversed micelles in the organic solvent;
  (2) then agitating the two-phase system for a period sufficient to produce an ion pair complex of the pre-activated enzyme and the ionic surfactant and to extract the ion pair complex directly from the aqueous solution into solution in the organic extraction solvent, without substantial formation of reversed micelles;
  (3) then separating the organic phase from the aqueous phase, whereby a homogeneous organic enzyme solution is obtained containing dissolved pre-activated enzyme-surfactant ion pair complex and essentially no reversed micelles.

3. The method of claim 2, further comprising, after the separating step, the step of drying the organic extraction solvent.

4. The method of claim 2, further comprising, after the separating step, the step of evaporating the organic extraction solvent.

5. The method of claim 2, in which the enzyme is α-chymotrypsin, the surfactant is Aerosol OT, AOT, the pH of the aqueous activating solution is form about 7.0 to about 8.5, the ionic strength is less tan about 20 mM, the enzyme:surfactant ratio is about 1:30 and the enzyme surfactant ion pair has a catalytic efficiency $k_{cat}/K_M$ in isooctane for the transesterification of N-acetyl-L-phenylalinine ethyl ester with 1-propanol of greater tan 3000 $M^{-1}S^{-1}$.

6. The method of claim 2, in which the volumes of aqueous solution and organic extraction solvent are about equal, the starting concentration of the surfactant in the organic solvent is about 2 mM, and the starting concentration of the enzyme in the aqueous solvent 1 mg/ml.

7. The methods claim 2 in which the surfactant is cationic and the pH of maximum activity is above the pl of the enzyme.

8. The method of claim 2, wherein the ratio of surfactant to enzyme is less than about half of the reversed micelle ratio.

9. The method of claim 2, wherein the ratio of surfactant to enzyme is between about one tenth and about one half of the reversed micelle ratio.

10. The method of claim 1, wherein conversion of the at least one substrate to the product is substantially completed before recovering a product.

11. The method of claim 10, further comprising, after step (d), precipitating the enzyme from the organic solvent by removal of the surfactant from the enzyme-surfactant complex.

12. The method of claim 1, in which the at least one substrate comprises an acyl donor and a nucleophile.

13. The method of claim 12 in which the acyl donor is a methyl or ethyl ester of tyrosine, tryptophan, alanine, or phenylalanine; a methyl or ethyl ester of a dipeptide or tripeptide containing any of tyrosine, tryptophan, alanine, or phenylalanine; or an N-benzoyl, N-acetyl, or N-carbobenzoxy derivative thereof; and the nucleophile is an amino acid amide.

14. The method of claim 12, in which the acyl donor and nucleophile are unblocked.

15. The method of claim 12, in which the acyl donor and nucleophile are added in a ratio between about 2:1 and 1:2.

16. The method of claim 1, in which the at least one substrate comprises at least one of an amino acid, an amino acid ester, an N-blocked amino acid, an N-blocked amino acid ester, an amino acid amide, an N-blocked amino acid amide, a polypeptide, a polypeptide ester, an N-blocked polypeptide, an N-blocked polypeptide ester, a polypeptide amide, and an N-blocked polypeptide amide.

17. The method of claim 1, in which the water content of the organic reaction solvent does not exceed the water saturation point for the organic solvent containing the surfactant.

18. The method of claim 1, in which the molar ratio of water to enzyme in the organic reaction solvent is less than about 75:1.

19. The method of claim 1, further comprising adding up to 0.2% v/v water to the reaction solvent.

20. The method of claim 1, in which the organic reaction solvent of (b) comprises of water miscible hydrophilic organic solvent.

21. The method of claim 1 in which the enzyme is a catalytic antibody, an oxidoreductases, a transferase, a lyase, an isomerase, or a ligase.

22. The method of claim 1 in which the enzyme is a hydrolase with acyl transferase activity in organic solvents.

23. The method of claim 1 in which the enzyme is a peroxidase catalyzing phenolic polymerizations, a tyrosinase catalyzing aromatic hydroxylations, an alcohol dehydrogenase catalyzing stereoselective oxidation and reduction, a lipase, a nuclease, an aldolase, a phosphatase, or a sulfatase.

24. The method of claim 1 in which the enzyme is subtilisin, papain, pepsin, thermolysin, or thrombin.

25. The method of claim 1, wherein the at least one substrate is added to the organic reaction solvent continuously during conversion of the at least one substrate to a product.

26. The method of claim 1, wherein the product is removed from the organic reaction solvent continuously during conversion of the at least one substrate to a product.

27. The method of claim 1, wherein the conversion is carried out as a batch process.

28. The method of claim 1, wherein the organic reaction solvent comprises an organic solvent and water in an amount sufficient to maximize the yield of catalysis.

29. The method of claim 1, wherein the ratio of surfactant to enzyme is less than about 90/110 of the reversed micelle ratio.

30. A catalyst produced by a process comprising (1) forming a two-phase aqueous/organic system comprising (a) a pro-activated enzyme solution produced by dissolving an enzyme in an aqueous solution at a pH of maximal enzyme activity, an enzyme concentration of from about 1 µg/ml to about 10 mg/ml, and ionic strength less than about 80 mM, (b) an organic extraction solvent that is immiscible with water, and (c) an ionic surfactant, the molar ratio of surfactant to enzyme in the two-phase system being sufficient to form an enzyme-surfactant ion pair complex, and substantially less than that necessary to form reversed micelles in the organic solvent; (2) then agitating the two-phase system for a period sufficient to produce an ion pair complex of the activated enzyme and the ionic surfactant and to extract the ion pair complex directly from the aqueous solution into solution in the organic extraction solvent, without substantial formation of reversed micelles, (3) then separating the organic phase from the aqueous phase, whereby a homogeneous organic enzyme solution is obtained containing dissolved pro-activated enzyme-surfactant ion. pair complex and essentially no reversed micelles, the pre-activated enzyme having catalytic efficiency at least an order of magnitude greater than a suspension of an equal amount of the enzyme in the organic solvent without surfactant.

31. The catalyst of claim 30, wherein the catalyst is further converted to a solid having water content of about 5% to about 10% by weight.

32. The catalyst of claim 30, wherein the ratio of surfactant to enzyme is less than about half of the reversed micelle ratio.

33. The catalyst of claim 30, wherein the ratio of surfactant to enzyme is between about one tenth and about one half of the reversed micelle ratio.

34. The catalyst of claim 30, wherein the ratio of surfactant to enzyme is less than about 80% of the stoichiometric amount necessary to fully cover the enzyme with surfactant.

35. The catalyst of claim 30, wherein the ratio of surfactant to enzyme is less than about 90/110 of the reversed micelle ratio.

36. The catalyst of claim 30, wherein the catalytic efficiency is at least two orders of magnitude greater than a suspension of an equal amount of the enzyme and organic solvent without surfactant.

37. A catalyst according to claim 30, having catalytic efficiency at least about 1.5% of an aqueous solution of the enzyme at a pH of maximal activity.

38. The catalyst of claim 37, wherein the catalytic efficiency is at least about 15% of an aqueous solution of the enzyme at a pH of maximal activity.

39. A method of producing a catalyst comprising:
  (1) forming a two-phase aqueous/organic system comprising (a) a pre-activated enzyme solution produced by dissolving an enzyme in an aqueous solution at a pH of maximal enzyme activity, (b) an organic extraction solvent that is immiscible with water, and (c) an ionic surfactant, the molar ratio of surfactant to enzyme in the two-phase system being sufficient to form an enzyme-surfactant ion pair complex, and substantially less than that necessary to form reversed micelles in the organic solvent;
  (2) then agitating the two-phase system for a period sufficient to produce an ion pair complex of the pre-activated enzyme and the ionic surfactant and to extract the ion pair complex directly from the aqueous solution into solution in the organic extraction solvent, without precipitation or substantial formation of reversed micelles, such that the ion pair complex has catalytic efficiency ($k_{cat}/K_m$, at least one order of magnitude greater than an equal amount of the enzyme suspended in the organic solvent; and
  (3) then separating the organic phase from the aqueous phase, whereby a homogeneous organic enzyme solution is obtained containing the dissolved pre-activated enzyme-surfactant ion pair complex and essentially no reversed micelles.

40. A method according to claim 39 in which the ion pair complex has catalytic efficiency at least two orders of magnitude greater than an equal amount of the enzyme suspended in the organic solvent.

41. A method according to claim 39 in which the ion pair complex has catalytic efficiency at least three orders of magnitude greater than an equal amount of the enzyme suspended in the organic solvent.

* * * * *